United States Patent [19]
Sun et al.

[11] Patent Number: 6,077,319
[45] Date of Patent: Jun. 20, 2000

[54] PROCESSES FOR PREPARING MICROBIOCIDAL TEXTILES

[75] Inventors: Gang Sun; Xiangjing Xu, both of Davis, Calif.

[73] Assignee: The Regents of The University of California, Oakland, Calif.

[21] Appl. No.: 09/102,525

[22] Filed: Jun. 22, 1998

Related U.S. Application Data

[62] Division of application No. 08/713,406, Sep. 13, 1996, Pat. No. 5,882,357.

[51] Int. Cl.$^7$ .................................................. D06M 13/35
[52] U.S. Cl. ............................... 8/189; 8/115.51; 8/115.7
[58] Field of Search ........................ 8/108.1, 189, 115.69, 8/115.51, 115.7; 510/302, 319, 383; 424/404, 405; 252/8.86

[56] References Cited

U.S. PATENT DOCUMENTS

| | | | |
|---|---|---|---|
| 2,950,553 | 8/1960 | Hurwitz | 8/183 |
| 3,061,469 | 10/1962 | Manowitz et al. | 8/189 |
| 3,401,005 | 9/1968 | Katz | 8/189 |
| 3,445,279 | 5/1969 | Abrahams et al. | 117/143 |
| 3,488,701 | 1/1970 | Herbes et al. | 8/189 |
| 3,565,824 | 2/1971 | Pierce, Jr. et al. | 252/429 |
| 3,576,591 | 4/1971 | Cusano | 8/185 |
| 3,594,113 | 7/1971 | Lifland et al. | 8/115.6 |
| 3,650,667 | 3/1972 | Luechauer | 8/111 |
| 3,674,811 | 7/1972 | Kern | 8/189 |
| 3,812,201 | 5/1974 | Bey | 525/418 |
| 4,199,322 | 4/1980 | Danna et al. | 8/186 |
| 4,306,872 | 12/1981 | Herbes et al. | 8/189 |
| 4,585,650 | 4/1986 | Newberry, Jr. et al. | 424/73 |
| 4,844,891 | 7/1989 | Rosen et al. | 424/76.4 |
| 5,104,649 | 4/1992 | Jansson et al. | 424/78.31 |
| 5,208,016 | 5/1993 | Ohmae et al. | 424/78.27 |
| 5,221,574 | 6/1993 | Branch et al. | 428/289 |
| 5,352,693 | 10/1994 | Farina | 514/398 |
| 5,405,862 | 4/1995 | Farina et al. | 514/389 |
| 5,490,983 | 2/1996 | Worley et al. | 424/405 |
| 5,610,189 | 3/1997 | Whiteley | 514/557 |
| 5,707,404 | 1/1998 | Andrews et al. | 8/189 |

FOREIGN PATENT DOCUMENTS

| | | |
|---|---|---|
| 2500430 | 7/1975 | Germany . |
| 4125431 | 7/1992 | Germany . |
| 2161399 | 1/1986 | United Kingdom . |

OTHER PUBLICATIONS

Gagliardi et al., "Antibacterial Finishes,"*American Dyestuff Reporter* 2:31–40 Jan. (1962).
Rigby et al., "Medical Textiles —Textiles Materials in Medicine and Surgery," *Textile Horizons* 42–45 (1993). No month available.
Sun et al., "A New Cyclic N–Halamine Biocidal Polymer," *Ind. Eng. Chem. Res.* 33:168–170 (1994). No month available.
Vigo, "Antimicrobial Fibers and Polymers," *Manmade Fibers: Their Origin and Development* 214–226 (1992). No month available.
Vigo, "Advances in Antimicrobial Polymers and Materials," *Biotechnology and Bioactive Polymers*, Eds. Gebelein and Carraher, Plenum Press, New York 225–237 (1994). No month available.
Worley et al., "Biocidal Polymers," *Trends in Polymer Science* 4(11):364–370 Nov. (1996). No month available.
Chemical Abstracts No. 78:73517u (1973), No month available.

*Primary Examiner*—Caroline D. Liott
*Attorney, Agent, or Firm*—Townsend and Townsend and Crew LLP

[57] ABSTRACT

The present invention provides durable and regenerable microbiocidal textiles and methods for preparing same. Such textiles can be readily prepared using a wet finishing process to covalently attach a hetercyclic N-halamine to a cellulose based material or other polymeric material. Once prepared, the textiles of the present invention have a broad spectrum of biocidal activity against pathogenic microorganisms. Moreover, the biocidal activity of such textiles can be regenerated by washing with a halogenated solution.

16 Claims, 2 Drawing Sheets

2,2,5,5-TETRAMETHYL-1,3-IMIDAZOLIDIN-4-ONE       6,6-DIMETHYL-1,3,5-TRIAZINE-2,4-DIONE 4,4,5,5-TETRAMETHYL-1,3-IMIDAZOLIDIN-2-ONE    CYANURIC ACID    5,5-DIMETHYLHYDANTOIN

MONOMETHYLOL-5,5-DIMETHYLHYDANTOIN (MDMH)    1,3-DIMETHYLOL-5,5-DIMETHYLHYDANTOIN (DMDMH)

MONOMETHOXYMETHYL-5,5-DIMETHYLHYDANTOIN    1,3-DIMETHOXYMETHYL-5,5-DIMETHYLHYDANTOIN 6,077,319

PROCESSES FOR PREPARING MICROBIOCIDAL TEXTILES

This application is a division of and claims the benefit of U.S. application Ser. No. 08/713,406, filed Sep. 13, 1996, now U.S. Pat. No. 5,882,357, the disclosure of which is incorporated by reference.

BACKGROUND OF THE INVENTION

An important and growing part of the textile industry is the medical and related healthcare and hygiene sectors. Textile materials used in medical-related applications include, for example, surgeon's gowns, caps and masks, patient drapes, bandages, wipers and cover cloths of various sizes. Such textile materials, however, are conductive to cross-infection and transmission of diseases caused by microorganisms. As such, the possibility of spreading infections caused by the lethal HIV virus, the insidious hepatitis virus or other epidemic diseases has created an increased concern regarding the use of protective facilities and uniforms for workers in the medical/healthcare/hygiene sectors. Currently, textile materials used in medical applications are disposable, nonwoven synthetic fabrics which are neither biocidal nor reusable. Such textile fabrics provide protection by blocking the transmission of microorganisms, rather than by inhibiting the growth of the microorganisms. Thus, cross-infection through surface contact of the contaminated textile fabrics is problematic. As a result, in an effort to prevent the cross-infection and transmission of diseases, the contaminated materials must be appropriately sterilized and discarded after use. Unfortunately, such sterilization and discarding procedures result in substantial increases in the cost of healthcare and in the amount of bio-hazardous wastes that are generated.

Accordingly, it is desirable that bacterial infections resulting from contact with contaminated textiles be reduced or eliminated, and that transmission of pathogenic bacteria from person to person during wear or use of contaminated textiles be prevented by inhibiting the growth of the microorganisms on fabrics. Moreover, it is desirable that surgeon's dresses, hospital carpeting and bedding materials, underwear, socks, and uniforms be biocidal so as to provide the best protection possible. In addition, it is desirable to have biocidal textiles for use in, inter alia, hotel-use towels, bedding materials, socks and other hygienic products as well.

Currently, there are two general categories of technologies which can provide protection for medical/healthcare/hygiene personnel. They are (1) physical techniques which involve the formation of a physical barrier against microbial infiltration or transmission by selecting fabric constructions and coating that are impermeable or that are microporous and contain antimicrobial agents; and (2) chemical technologies which involve the incorporation of active functional agents onto fabrics or fibers by grafting or other chemical methods. Disposable materials are examples of the first category. The coating method involves the application of impermeable materials onto the surface of fabrics, thereby blocking the infiltration and permeation of microorganisms. However, cross-infection and spreading of diseases through the contact of the coating surface is still feasible and, thus, pose potential threats to workers who handle the contaminated materials. Moreover, the impermeable properties can cause wearers to become uncomfortable and, in turn, to become less efficient in their.

As such, the chemical association of antibacterial agents onto either the surface or entirety of the material appears to be more practical in terms of durability and efficacy of the antibacterial properties. There are two major pathways to chemically achieve durable antibacterial effects. In one pathway, the slow-releasing of biocides through contact with the processed fabrics is employed. In this pathway, a pathway widely used around the world, sufficient chemical agents are impregnated onto the fibers by either chemical or physical methods. Thereafter, the biocides are slowly released from the processed fabrics into the media, thereby contacting and inhibiting the growth of microorganisms. Unfortunately, such chemical agents can be washed away easily if they are not covalently impregnated onto the surface of the fabrics. Moreover, the antibacterial functions are non-regenerable.

In the second pathway, a more innovative technology is employed which involves chemical modification of textile materials with biocidal or potential biocidal compounds, wherein the antibacterial properties of such compounds are regenerable with a simple washing. The potential antibacterial groups can be rendered biocidal after washing with certain common chemicals, such as diluted bleaching solutions. Over thirty-five years ago, Gagliardi, et al. first proposed the regeneration principle of antibacterial finishing, hoping to regenerate the lost function by washing the used fabrics with some specific solutions (see, *Am. Dyest. Reptr.,* 51, 49 (1962). However, although much effort has been expended, no commercial products have resulted.

In view of the foregoing, there exists a need in the art for durable and regenerable microbiocidal textiles. The present invention remedies such need by providing, inter alia, durable and regenerable microbiocidal textiles.

Two commercially available heterocyclic compounds with same active moieties have been applied on cotton and cotton containing materials. These compounds are soluble in water, so an aqueous finishing process is adopted. The chemicals were padded on fabrics, and then dried and cured at elevated temperatures. The biocidal properties of finished cotton fabrics have been evaluated against *Escherichia coli.* and *Staphylococcus aureus* mainly. Qualitative biocidal tests of the research have been summarized in a conference proceeding.

SUMMARY OF THE INVENTION

The present invention provides, inter alia, durable and regenerable microbiocidal textiles and methods for preparing same. Such textiles can be readily prepared using a classical wet finishing process to covalently attach a heterocyclic N-halamine to a cellulose based material or other polymeric material. Once prepared, the textiles of the present invention have a broad spectrum of biocidal activity against pathogenic microorganisms. Moreover, the biocidal activity of such textiles can be regenerated by washing with a halogenated solution.

In one embodiment, the present invention provides a process for preparing a microbiocidal cellulosic, cellulosic/polyester or polyester textile precursor, the process comprising: (a) immersing a cellulosic, cellulosic/polyester or polyester textile in an aqueous treating solution which comprises a heterocyclic N-halamine, a wetting agent and a catalyst; (b) removing the excess treating solution from the cellulosic, cellulosic/polyester or polyester textile; (c) drying the cellulosic, cellulosic/polyester or polyester textile; (d) curing the dried cellulosic, cellulosic/polyester or polyester textile; (e) washing the cured cellulosic, cellulosic/polyester or polyester textile to remove excess reagents; and (f) drying the treated cellulosic, cellulosic/polyester or polyester textile to remove water.

In another embodiment, the present invention provides a process for rendering a cellulosic, cellulosic/polyester or polyester textile microbiocidal, the process comprising: (a) washing a microbiocidal cellulosic, cellulosic/polyester or polyester textile precursor with a halogenated solution, the microbiocidal textile precursor being prepared in accordance with the above method; and (b) drying the treated microbiocidal cellulosic, cellulosic/polyester or polyester textile to remove water. In the process, the halogenated solution can be a chlorine solution or, alternatively, a bromine solution. In a presently preferred embodiment, the halogenated solution is a chlorine solution (e.g., a chlorine bleach solution such as Clorox). The washing of the microbiocidal cellulosic, cellulosic/polyester or polyester textile precursor with a halogenated solution renders the textile biocidal and, in addition, it sterilizes the textile.

In yet another embodiment, the present invention provides a composition for finishing fabrics, i.e., an aqueous treating solution, the composition comprising a wetting agent; and a heterocyclic N-halamine. In a preferred embodiment, the composition further includes a catalysts. In an even more preferred embodiment, the composition further includes additives (e.g., softeners and waterproofing agents) to impart favorable characteristics.

There are a myriad of applications areas for the microbiocidal textiles of the present invention. For instance, the microbiocidal textile materials can provide biocidal protective clothing to personnel in the medical area as well as in the related healthcare and hygiene area. In contrast to previously used textiles, the textiles of the present invention are not a barrier to microorganisms, but rather a disinfectant to them. As such, the regenerable and reusable biocidal materials can replace currently used disposable, nonwoven fabrics as medical textiles, thereby significantly reducing hospital maintenance costs and disposal fees. The microbiocidal properties of the textiles of the present invention can be advantageously used for women's wear, underwear, socks, and other hygienic purposes. In addition, the microbiocidal properties can be imparted to paper or carpeting materials to create odor-free and germ-free carpets. Moreover, all germ-free environments, such as required in biotechnology and pharmaceutical industry, would benefit from the use of the microbiocidal textiles of the present invention to prevent any contamination from air, liquid, and solid media.

Other features, objects and advantages of the invention and its preferred embodiments will become apparent from the detailed description which follows.

DETAILED DESCRIPTION OF THE INVENTION AND PREFERRED EMBODIMENTS

Figure 1:
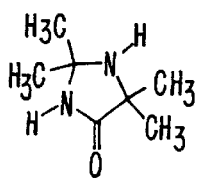
FIG. 1 illustrates examples of heterocyclic N-halamines which are suitable for use in the present invention.
Figure 1:
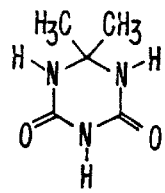
Figure 1:
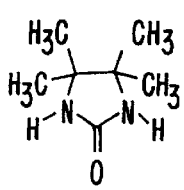
Figure 1:
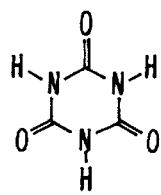
Figure 1:
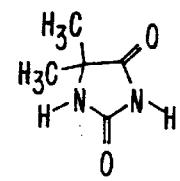
Figure 1:
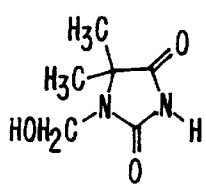
Figure 1:
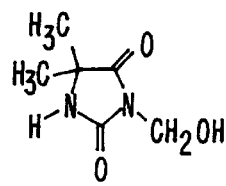
Figure 1:
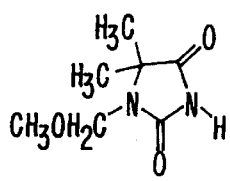
Figure 1:
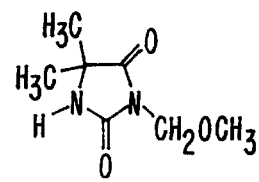
Figure 1:
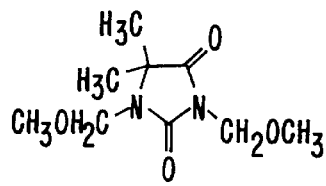
Figure 2:
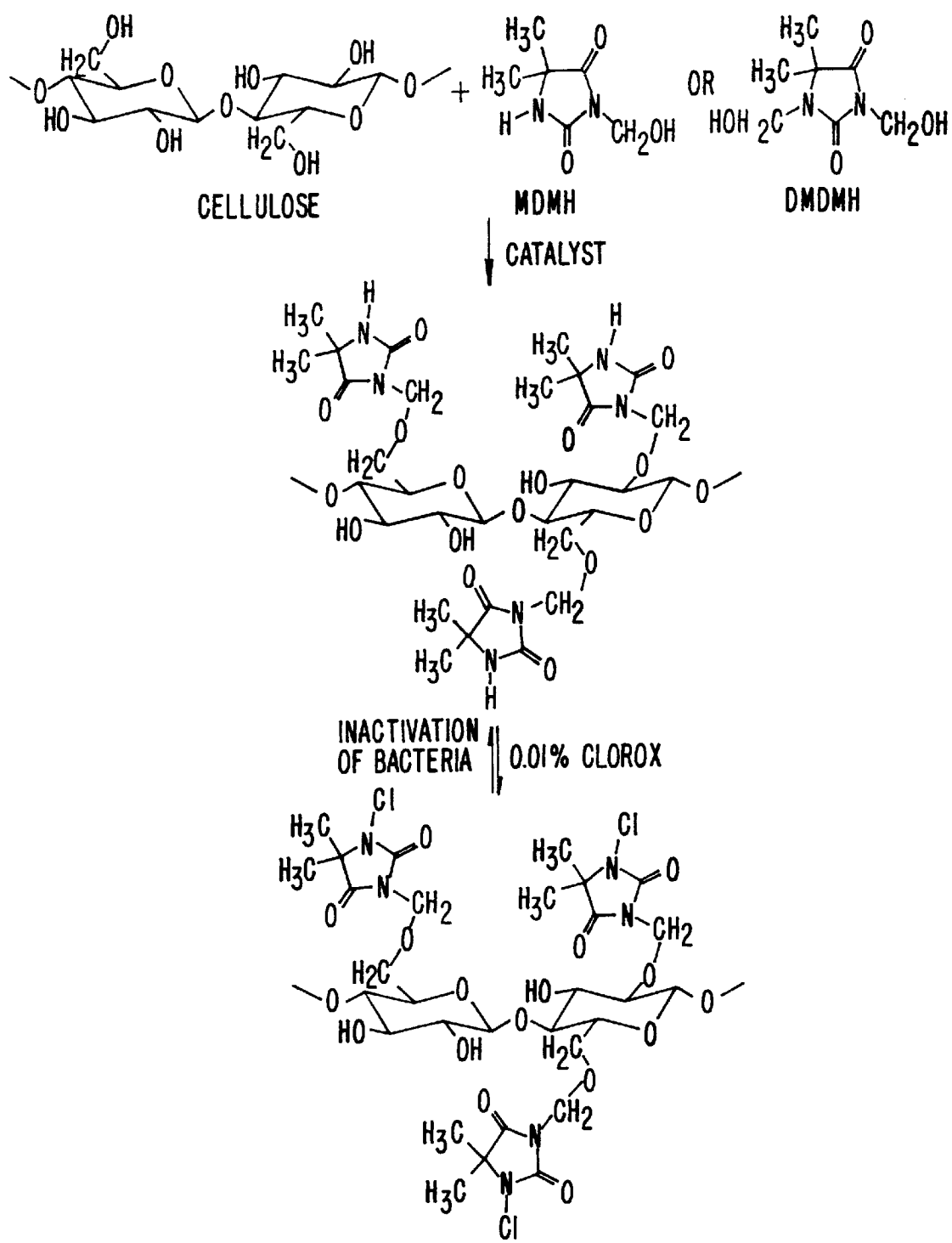
FIG. 2 illustrates the reaction scheme whereby the heterocyclic N-halamine is covalently attached to cellulose.

In one embodiment, the present invention provides a process for preparing a microbiocidal cellulosic, cellulosic/polyester or polyester textile precursor, the process comprising: (a) immersing a cellulosic, cellulosic/polyester or polyester textile in an aqueous treating solution which comprises a heterocyclic N-halamine, a wetting agent and a catalyst; (b) removing the excess treating solution from the cellulosic, cellulosic/polyester or polyester textile; (c) drying the cellulosic, cellulosic/polyester or polyester textile; (d) curing the dried cellulosic, cellulosic/polyester or polyester textile; (e) washing the cured cellulosic, cellulosic/polyester or polyester textile to remove excess reagents; and (f) drying the treated cellulosic, cellulosic/polyester or polyester textile to remove water.

"Heterocyclic N-halamine," as used herein, refers to a 4- to 7-membered ring, wherein at least 3 members of the ring are carbon, and from 1 to 3 members of the ring are nitrogen heteroatom, and from 0 to 1 member of the ring is oxygen heteroatom, wherein from 0 to 2 carbon members comprise a carbonyl group, and wherein at least 1 to 3 nitrogen atoms are substituted with a hydrogen or hydroxyalkyl group, such as —$CH_2OH$, or a alkoxyalkyl group, such as —$CH_2OCH_3$. At least one ring nitrogen has bonded thereto a halogen atom. In addition, the ring members can be further substituted with alkyl groups, such as methyl, ethyl, etc., or hydroxy groups. Heterocyclic N-halamines are generally disclosed in U.S. Pat. No. 5,490,983 issued to Worley, et al. on Feb. 13, 1996, the teachings of which are incorporated herein by reference for all purposes.

Heterocyclic N-halamines suitable for use in accordance with the present invention include, but are not limited to, the following: the halogenated product of monomethylol-5,5-dimethylhydantoin (MDMH), 1,3-dimethylol-5,5-dimethylhydantoin (DMDMH); monomethylolated and dimethylolated derivatives of 2,2,5,5-tetramethyl-1,3-imidazolidin-4-one, 6,6-dimethyl-1,3,5-triazine-2,4-dione, 4,4,5,5-tetramethyl-1,3-imidazolidin-2-one, cyanuric acid and 5,5-dimethylhydantoin; and monomethoxylated and dimethoxylated derivatives of monomethylolated and dimethylolated derivatives of 6,6-dimethyl-1,3,5-triazine-2,4-dione, 4,4,5,5-tetramethyl-1,3-imidazolidin-2-one, cyanuric acid, 5,5-dimethylhydantoin and 2,2,5,5-tetramethyl-1,3-imidazolidin-4-one. Examples of the monomethoxylated and dimethoxylated compounds are monomethoxymethyl-5,5-dimethylhydantoin and 1,3-dimethoxymethyl-5,5-dimethylhydantoin, respectively. In a presently preferred embodiment, monomethylol-5,5-dimethylhydantoin and 1,3-dimethylol-5,5-dimethylhydantoin are the heterocyclic N-halamines employed.

Precursors to heterocyclic N-halamines used in the present invention are commercially available from a number of different sources. For instance, monomethylol-5,5-dimethylhydantoin (MDMH) and 1,3-dimethylol-5,5-dimethylhydantoin (DMDMH) are commercially available under the tradenames DANTOIN® and GLYDANT® XL-1000, respectively, from LONZA, INC. (Fair Lawn, N.J.). Moreover, cyanuric acid is commercially available from ALDRICH® (Milwaukee, Wis.). In addition, those of skill in the art will readily appreciate that the heterocyclic N-halamines used in the present invention can be synthesized in a variety of ways using conventional synthetic chemistry techniques. In this connection, those of skill will readily appreciate that the dimethoxylated derivatives are prepared from the dimethylated derivatives, whereas the monomethoxylated derivatives are prepared from either the mono- or dimethylated derivatives.

Examples of precursors of the heterocyclic N-halamines suitable for use in the present invention are set forth in FIG. 1. It should be noted that many of these precursors to heterocyclic N-halamines are widely used in cosmetic products and their halogenated derivatives are major disinfectants for use in, for example, swimming pools. As such, these compounds will not generate any toxic effects for humans or for the environment either in terms of the finished fabric or during the finishing process.

"Microbiocidal," as used herein, refers to the ability to kill at least some types of microorganisms, or to inhibit the growth or reproduction of at least some types of microorganisms. The textiles prepared in accordance with the present invention have microbiocidal activity against a broad spectrum of pathogenic microorganisms. For example, such textiles have microbiocidal activity against representative gram-positive (such as *Staphylococcu aureus*) and gram-negative bacteria (such as *Eschenchia coli*). Moreover, the microbiocidal activity of such textiles is readily regenerable.

In step (a) of the above process, the aqueous treating solution comprises a heterocyclic N-halamine as described above, a wetting agent and a catalyst. As used herein, "wetting agent" refers to a substance that increases the rate at which a liquid spreads across a surface, i.e., it renders a surface nonrepellent to a liquid. Examples of suitable wetting agents include, but are not limited to, TRITON® X-100 (generically, octylphenoxypolyethoxyethanol) (Sigma Chemical Co., St. Louis, Mo.), SEQUAWET® (generically, a nonionic dispersant) (Sequal Chemical Inc., Chester, S.C.), and AMWET® (generically, a wetting agent, detergent, penetrant for textile processing) (American Emulsions Co., Dalton, Ga.). Other wetting agents suitable for use in the present invention will be known to and used by those of skill in the art. As used herein, "catalyst" refers to a substance which augments the rate of a chemical reaction without itself being consumed. Suitable catalysts for use in the present invention include, but are not limited to, the following: magnesium salts, zinc salts and ammonium salts. In a presently preferred embodiments, the catalyst employed is one of the following: $MgCl_2$, $Mg(NO_3)_2$, $Zn(NO_3)_2$ and $NH_4NO_3$.

Those of skill in the art will readily appreciate that the concentration of the various components of the aqueous treating solution can be widely varied depending upon the particular components employed and the results desired. Typically, the heterocyclic N-halamine is present at a concentration of at least about 0.2%. More typically, the heterocyclic N-halamine is present at a concentration ranging from about 0.2% to about 20%, more preferably at a concentration ranging from about 0.5% to about 10% and, more preferably at a concentration ranging from about 1% to about 5%. It will be readily apparent to those of skill in the art that higher heterocyclic N-halamine concentrations (e.g., 50%) can be employed, but such higher concentrations are not required to impart microbiocidal activity. Again, suitable microbiocidal activity can be imparted using a heterocyclic N-halamine concentration as low as about 0.2%. The wetting agent is typically present at a concentration ranging from about 0.1% to about 3% and, more preferably, at a concentration ranging from about 0.2% to about 1%. The concentration of the catalyst employed will depend on the concentration of the heterocyclic N-halamine employed. Typically, the ratio of heterocyclic N-halamine to catalyst present will range from about 10:1 to about 5:1. The pH of the aqueous treating solution will typically range from a pH of about 2 to about 6 and, more preferably, from a pH of about 2.5 to about 4.5.

Those of skill in the art will readily appreciate that other additives can be incorporated into the aqueous treating solution to impart favorable characteristics to the cellulosic, cellulosic/polyester or polyester textile. Such additives can include softeners and waterproofing agents which are known to and used by those of skill in the art. Examples of softeners which can be added to the aqueous treating solution include, but are not limited to, MYKON® and SEQUASOFT®, both of which are commercially available from Sequal Chemical Inc. (Chester, S.C.). Examples of waterproofing agents which can be added to the aqueous treating solution include, but are not limited to, SEQUAPEL® (Sequal Chemical Inc., Chester, S.C.), SCOTCHGARD (3M, St. Paul, Minn.) and other water repellent finishing solutions used by those of skill in the art.

In carrying out step (a), the textile used may be roving, yarn or fabric regardless of whether spun, knit, or woven, or may be nonwoven sheets or webs. Moreover, the textile may be made of cellulosic fibers, polyester fibers or blends of these. In addition, other polymer materials having reactive functional groups (e.g., —OH groups) can be used. Such polymer materials include, but are not limited to, polyvinyl alcohol (PVA), starches and proteins. In wetting the textile in the finshing or treating bath, ordinary textile equipment and methods suitable for batchwise or continuous passage of roving, yarns or fabrics through an aqueous solution may be used, at any speed permitting thorough and uniform wetting of the textile material.

In step (b), the excess aqueous treating solution is removed by ordinary mechanical methods such as by passing the textile between squeeze rolls, by centrifugation, by draining or by padding. In a preferred embodiment, the excess aqueous treating solution is removed by padding.

In step (c), the cellulosic, cellulosic/polyester or polyester textile is dried at a temperature ranging from about 50° C. to about 90° C. and, more preferably, at a temperature ranging from about 75° C. to about 85° C. for a period of time ranging from about 3 to about 8 minutes and, more preferably, for about 5 minutes.

In step (d), the dried cellulosic, cellulosic/polyester or polyester textile is cured at a temperature ranging from about 120° C. to about 180° C. and, more preferably, at a temperature ranging from about 140° C. to about 160° C. for a period of time ranging from about 3 to about 8 minutes and, more preferably, for about 5 minutes. The heating can be carried out in an oven, preferably one having a forced draft of air directed at the surface of the textile and exhausting through a vent to remove fumes.

In step (e), the dried cellulosic, cellulosic/polyester or polyester textile is washed. Washing of the treated textile, step (d), may be done with either hot or cold water. The covalent bonds formed are stable, insoluble, and durable to the mechanical agitation, spraying and rubbing that occurs in washing machines or in large scale continuous or batchwise textile washing equipment.

Final drying, step (f), can be carried out by any ordinary means such as oven drying, line drying or tumble drying in a mechanical clothes dryer. A drying temperature of about 80° to about 120° C. for about 1 to about 5 minutes is particularly preferred.

In another embodiment, the present invention provides a process for rendering a cellulosic, cellulosic/polyester or polyester textile microbiocidal, the process comprising: (a) washing a microbiocidal cellulosic, cellulosic/polyester or polyester textile precursor with a halogenated solution, the microbiocidal textile precursor being prepared in accordance with the above method; and (b) drying the treated microbiocidal cellulosic, cellulosic/polyester or polyester textile to remove water. In the process, the halogenated solution can be a chlorine solution or, alternatively, a bromine solution. In a presently preferred embodiment, the halogenated solution is a chlorine solution (e.g., a chlorine bleach solution such as CLOROX®). The washing of the microbiocidal cellulosic, cellulosic/polyester or polyester textile precursor with a halogenated solution renders the textile biocidal and, in addition, it sterilizes the textile.

Moreover, as previously explained, the microbiocidal activity, i.e., oxidative properties, of the textiles can be regenerated by periodically washing the textile with a halogenated solution during regular washings.

In yet another embodiment, the present invention provides a composition for finishing fabrics, the composition comprising a wetting agent; and a heterocyclic N-halamine. In a preferred embodiment, the composition further includes a catalysts. In an even more preferred embodiment, the composition further includes additives (e.g., softeners and waterproofing agents) to impart favorable characteristics. The discussions pertaining to the heterocyclic N-halamines, wetting agents, catalysts, additives and their various concentrations are fully applicable to this composition and, thus, such discussions will not be repeated again. The pH of the aqueous treating solution will typically range from a pH of about 2 to about 6 and, more preferably, from a pH of about 2.5 to about 4.5. Those of skill in the art will readily appreciate that the above composition can be prepared in a concentrated form or, alternatively, in a form suitable for immediate use, i.e., at appropriate reagent concentrations.

Considering both antibacterial and mechanical properties of the finished textiles prepared using the methods and compositions set forth herein, those of skill will readily appreciate that such finished textiles can advantageously be used in the preparation of the following articles: surgeon's gowns, caps, masks, surgical cover, patient drapes, carpeting, bedding materials, underwear, socks, uniforms, etc. Those of skill in the art will readily appreciate that the finished textiles of the present invention can also advantageously be used for a variety of other purposes, such as in hotel-use towels, bedding materials, hygienic products, in various clothing to protect against pesticides and other toxic chemicals, etc.

The invention will be described in greater detail by way of specific examples. The following examples are offered for illustrative purposes, and are intended neither to limit or define the invention in any manner.

EXAMPLES

Example I

This example illustrates the finishing of fabrics with monomethylol-5,5-dimethythydantoin (MDMH or Anti-1).

A finishing bath containing 24 grams of monomethylol-5,5-dimethylhydantoin, 4.8 grams magnesium chloride, and 0.6 gram of Triton X-100 (a wetting agent) in 600 milliliters of deionized water was prepared. The pH of the finishing bath was adjusted to 3.4 with one milliliter of 0.1 N HCl solution. Then, 140.9 grams of pure cotton fabric (#400 Testfabrics, Inc., Middlesex, N.J.) and 141.4 grams of cotton/polyester (35/65) blend fabric (#7409, Testfabrics, Inc., Middlesex, N.J.) were dipped in the bath for more than five minutes and padded through a padder with a more than 80% pick-up rate. The fabrics were dipped and padded again, and dried at 80° C. for 5 minutes. The fabrics were then cured at 160° C. for 5 minutes. Finally, the finished fabrics were machine washed with 90 grams of American Association of Textile Chemists and Colorists (AATCC) Standard Reference Detergent 124 at a low water level and a temperature of about 60° C. for 30 minutes. The fabrics were dried and weighed, yielding 42.8 grams (1.35% add-on) of the cotton fabric and 142.4 grams (0.71% add-on) of the cotton/polyester blend fabric. The cotton product exhibited prominent infrared adsorption bands in a KBr pellet at 1718 and 1770 cm$^{-1}$.

Thereafter, the finished fabrics were washed with a diluted Clorox solution containing about 0.01% active chlorine. Antibacterial properties of the fabrics were tested against representative gram-positive (such as *Staphylococcu aureus* (ATCC 5368)) and gram-negatibe bacteria (such as *Escherichia coli* (ATCC 2666)) using the protocol set forth in Example III.

Example II

This example illustrates the finishing of fabrics with 1,3-dimethylol-5,5-dimethylhydantoin (DMDMH or Anti-2).

A finishing bath containing 48 grams of 1,3-dimethylol-5,5-dimethylhydantoin (DMDMH or Anti-2), 9.6 grams magnesium chloride and 0.8 gram of Triton X-100 (a wetting agent) in 800 milliliters of deionized water was prepared. The pH of the finishing bath was adjusted to 3.1 with 20 milliliters of 0.01 N HCl solution. Then, 144.7 grams of pure cotton fabric (#400 Testfabrics, Inc., Middlesex, N.J.) and 143.2 grams of cotton/polyester (35/65) blend fabric (#7409, Testfabrics, Inc., Middlesex, N.J.) were dipped in the bath for more than five minutes and padded through a padder with more than an 80% pick up rate. The fabrics were dipped and padded again, and dried at 80° C. for 5 minutes. The fabrics were then cured at 160° C. for 5 minutes. Finally, the finished fabrics were machine washed with 90 grams of AATCC Standard Reference Detergent 124 at a low water level low and a temperature of about 60° C. for 30 minutes. The fabrics were dried and weighed, yielding 147.9 grams (2.22% add-on) of the cotton fabric and 145.5 grams (1.62% add-on) of the cotton/polyester blend fabric. The cotton product exhibited prominent infrared adsorption bands in a KBr pellet at 1718 and 1770 cm$^{-1}$.

Thereafter, the finished fabrics were washed with a diluted CLOROX® solution containing about 0.01% active chlorine. Antibacterial properties of the fabrics were tested against representative gram-positive (such as *Staphylococcu aureus* (ATCC 5368)) and gram-negatibe bacteria (such as *Escherichia coli* (ATCC 2666)) using the protocol set forth in Example III.

Example III

This example illustrates the qualitative antibacterial study of the Anti-1 finished fabrics carried out using the AATCC Test Method 147.

Fabric samples of #405 (pure cotton, Testfabrics, Inc., Middlesex, N.J.) and #7402 (cotton/polyester 35/65, Testfabrics, Inc., Middlesex, N.J.) were finished in a manner similar to that set forth in Example I. The concentration of the finishing agent used was from about 5 to 15% in the finishing of the cotton fabrics and from about 5 to 20% in the finishing of the cotton/polyester (35/65) blend fabric because of the lower concentration of cellulose in the blend. The final biocidal property was imparted onto the finished fabrics by washing them with a diluted CLOROX® solution containing 0.25% chlorine after each washing circle. Qualitative antibacterial tests were conducted according to AATCC Test Method 147.

In the AATCC Test Method 147, two pieces of chlorinated fabrics with the size of 25 mm×50 mm were placed on a nutrient agar plate which had been inoculated by five streaks of a diluted bacteria solution using a 4 mm inoculating loop. The diluted bacteria solution was prepared by transferring 1.0 milliliter of 24 hour broth culture into 9.0 milliliter of sterile distilled water. The agar plate was incubated at 37° C.

for 18–24 hours. The minimum width of inhibition zone along a streak on either side of the test specimen are measured. Table I sets forth the qualitative biocidal evaluations of the finished fabrics with different concentration of the agent Anti-1. Even with a 5% finishing agent concentration and about a 1% add-on of the agents, the processed fabrics exhibit durable and regenerable antibacterial properties.

TABLE I

Results of Finished Cotton (#405) and Cotton/Polyester 35/65 (#7402)

| Fabric | Conc. of Anti-1 (%) | Add-on % | Biocidal Results* After 20 Times Washing | | Biocidal Results After 50 Times Washing | |
|---|---|---|---|---|---|---|
| | | | E. coli | S. aureus | E. coli | S. aureus |
| #405 | 5 | 1.2 | >3 mm | >1 mm | >1 mm | ~1 mm |
| | 10 | 2.3 | >8 mm | >3 mm | >3 mm | >1 mm |
| | 15 | 3.1 | kill all | kill all | >4 mm | >4 mm |
| #7402 | 5 | 0.8 | >3 mm | >1 mm | >1 mm | ~1 mm |
| | 10 | 1.4 | >3 mm | >1 mm | >2 mm | ~1 mm |
| | 15 | 1.6 | kill all | kill all | >2 mm | >1 mm |
| | 20 | 2.0 | kill all | >4 mm | >3 mm | >1 mm |

*Biocidal results were tested with AATCC test method 147, the minimum disinfection distance is measured in millimeter (mm). Washing tests were conducted with machine wash warm according to AATCC test method 124 and AATCC Standard Reference Detergent 124 was used.

Example IV

Four types of clothing materials, i.e., #400, #7402 (35/65 cotton/polyester), Terry cloth and Rayon (all from Testfabrics, Inc., Middlesex, N.J.), were chemically finished with the functional agent following the protocol set forth in Example I. The antibacterial results of the different fabrics finished with Anti-1 are shown in Table II. The percentage of add-on of functional agents by the fabrics was only about 1%. However, after activation of the biocidal properties of the fabrics by washing the fabrics with diluted CLOROX®, the zones of inhabitation of bacteria were relatively large. The results indicate that the cellulose-containing materials can easily incorporate with the functional finishing agents and obtain the desired function against microorganisms in a broad spectrum. If complete disinfection is required, the add-on rate of the finishing agents could be increased by increasing the concentration of the agents as discussed above. However, in most applications, only appropriate biocidal properties are needed, especially in the anti-odor finshes.

TABLE II

Antibacterial Results of Different Fabrics Finished with Anti-1

| Fabrics | % Add-on of the agent | Biocidal results against S. aureus after being activated (mm) | Biocidal results against E. coli after being activated (mm) |
|---|---|---|---|
| Cotton cloth #400 | 1.43 | >1.0 | >2.0 |
| Rayon | 1.21 | >1.0 | >1.0 |
| Dacron/Cotton 65/35 #7402 | 1.19 | >4.0 | >10 |
| Terry cloth 100% Cotton | 1.40 | kill all | >10 |
| Control Cotton cloth #400 | — | all grow | all grow |

Example V

This example illustrates the quantitative antibacterial study (AATCC Test Method 100) of Anti-1 finished fabrics.

Quantitative studies of biocidal properties of the Anti-1 finished fabrics indicates that even at a very low concentration of the finishing bath, biocidal properties on fabrics can be obtained. AATCC Test Method 100 was adopted in this study. According to this test method, four pieces of staked circular fabric swatches 4.8±0.1 (about one grams) were inoculated with 1.0±0.1 milliliter of inoculum in a 250 milliliter jar. The inoculum was a nutrient broth culture containing over $1.0 \times 10^6$ clone forming units (CFU) of organisms. After the swatches were inoculated, they were neutralized by 100 milliliter of a 0.02% sodium thiosulfate solution in the jar. The contact time was the time between inoculation and neutralization. The jar was vigorously shaken and the neutralized solution was diluted in serial. The dilutions, usually $10^0$, $10^1$, and $10^2$, were plated on nutrient agar and incubated for 18–24 hours at 37° C. The number of bacteria recovered from the inoculated finished fabrics was counted and compared with that from untreated fabrics. Six log reduction means the total inactivation of bacteria, and one log reduction means that finished fabrics reduced bacteria counts from $10^6$ CFU to $10^5$ CFU. Finished fabrics prepared from solutions containing 1%–6% of monomethylol-5,5-dimethylhydantoin following the protocol set forth in Example 1 with pickup rates below 1% have been tested. The biocidal properties of such fabrics are set forth in Table III.

TABLE III

Effects of Finishing Concentrations of Anti-1 on Bacterial Reduction Rates.

| Conc. of agent Anti-1 | Material | Take up % | Bacterial reduction rates on contact time | | | | | |
|---|---|---|---|---|---|---|---|---|
| | | | 0 min | | 30 min | | 60 min | |
| | | | E. coli | S. aureus | E. coli | S. aureus | E. coli | S. aureus |
| 1% | #400 | 0.65 | No | No | No | 1 log | No | No |
| | #7402 | 0.14 | No | No | 1 log | No | 1 log | No |
| 2% | #400 | 0.03 | No | 1 log | 6 log | 6 log | 6 log | 6 log |
| | #7402 | 0.07 | No | No | 6 log | 1 log | 6 log | 6 log |
| 4% | #400 | 0.47 | 6 log | 6 log | 6 log | 6 log | 6 log | 6 log |
| | #7402 | 0.45 | 6 log | 6 log | 6 log | 6 log | 6 log | 6 log |
| 6% | #400 | 0.70 | 6 log | 6 log | 6 log | 6 log | 6 log | 6 log |
| | #7402 | 0.70 | 6 log | 6 log | 6 log | 6 log | 6 log | 6 log |

400 is 100% cotton plain woven fabric and #7402 is a 65/35 polyesterlcotton plain woven fabric. Six log reduction means total kill.

Table IV shows the effects of chlorine concentrations on biocidal properties of the antibacterial fabrics finished using the protocol set forth in Example 1. Every cycle of regeneration with different concentrations of chlorine will result in slight damages to the grafted heterocyclic rings. A concentration of 4% of monomethylol-5,5-dimethylhydantoin was selected as the finishing bath, and the take-up rate of the Anti-1 was 1.29%. The results obtained show some unexpected results for the #7402 fabric, which has more durable biocidal properties than cotton fabrics. Regeneration of the biocidal properties with lower chlorine concentration is preferred.

Fabrics finished with Anti-2 in accordance with the protocol set forth in Example II also exhibit durable press properties, which is understandable because the structure of DMDMH is very similar to that of 1,3-dimethylol-4,5-dihydroxylethylene urea (DMDHEU). Durable press properties were tested according to AATCC Test Method 66. In the tests, six warp specimens and six filling specimens of #400 cotton fabrics having the size of 15×40 mm were conditioned in a conditioning room (21±1° C. and 65±2% relative humidity) for over 24 hours. The wrinkle recovery angles of twelve samples which were creased with three warp and filling specimens on face side and three warp and filling specimens on back side were measured. Table VI shows the average wrinkle recovery angles of the finished fabrics after repeated washings. With higher concentration of the finishing agent, more functional agent are combined on the fabrics. Therefore, more cross-linking between cellulose chains will be formed and better wrinkle resistant properties of the fabrics will be expected.

TABLE IV

Effects of Chlorine Concentration on Biocidal Properties (Bacterial Reduction Rates)

| Cl % | Fabric | After five Washings | | After ten Washings | | After fifteen washings | | After twenty washings | |
|---|---|---|---|---|---|---|---|---|---|
| | | E. coli | S. aur. | E. coli | S. aur. | E. coli | S. aur. | E. coli | S. aur. |
| 0.01 | #400 | 6 log | 6 log | 6 log | 6 log | 6 log | 6 log | 6 log | 6 log |
| | #7409 | 6 log | 6 log | 6 log | 6 log | 6 log | 6 log | 6 log | 6 log |
| 0.1 | #400 | 6 log | 6 log | 6 log | 6 log | 6 log | 6 log | 1 log | 0 log |
| | #7409 | 6 log | 6 log | 6 log | 6 log | 6 log | 6 log | 6 log | 6 log |
| 0.25 | #400 | 6 log | 6 log | 2 log | 0 log | 1 log | 0 log | 1 log | 0 log |
| | #7409 | 6 log | 6 log | 6 log | 6 log | 6 log | 6 log | 1 log | 1 log |

400 is 100% cotton and #7409 is a 65/35 polyester/cotton blend. Contact time = 60 min. Six log reduction means total kill of bacteria. Zero log reduction means some reduction of bacterial growth and extended contact causes further reduction. Washing tests were following AATCC-124 using machine washing warm (140° C.) for 15 min. and 90 grams of AATCC detergent 124.

Example VI

This example illustrates the quantitative antibacterial study (AATCC Test Method 100) of Anti-2 finished fabrics.

Fabrics finished in accordance with the protocol set forth in Example II with Anti-2, i.e., 1,3-dimethylol-5,5-dimethylhydantoin, were also tested with AATCC test method 100, which was briefly described in Example IV. In the tests, a diluted CLOROX® solution containing 0.01% active chlorine was used to chlorinate the finished fabrics. The biocidal properties of Anti-2 finished fabrics are set forth in Table V.

TABLE VI

Wrinkle Recovery Angles of Anti-2 Finished #400 Pure Cotton Fabrics

TABLE V

Durable Antibacterial Properties of Anti-2 Finished Fabrics

| Conc of Anti-2 | Fabric | After five washes | | After ten washes | | After fifteen washes | | After twenty washes | | After twenty washes | |
|---|---|---|---|---|---|---|---|---|---|---|---|
| | | E. coli | S. aur. | E. coli | S. aur. | E. coli | S. aur. | E. coli | S. aur. | E. coli | S. aur. |
| 2% | #400 | 6 log | 6 log | 6 log | 6 log | 6 log | 6 log | 6 log | 6 log | 6 log | 6 log |
| | #7409 | 6 log | 6 log | 6 log | 6 log | 6 log | 6 log | 6 log | 6 log | 6 log | 6 log |
| 6% | #400 | 6 log | 6 log | 6 log | 6 log | 6 log | 6 log | 6 log | 6 log | 6 log | 6 log |
| | #7409 | 6 log | 6 log | 6 log | 6 log | 6 log | 6 log | 6 log | 6 log | 6 log | 6 log |
| 10% | #400 | 6 log | 6 log | 6 log | 6 log | 6 log | 6 log | 6 log | 6 log | 6 log | 6 log |
| | #7409 | 6 log | 6 log | 6 log | 6 log | 6 log | 6 log | 6 log | 6 log | 6 log | 6 log |

400 is 100% cotton and #7409 is a 65/35 polyester/cotton blend. Contact time = 60 min. Six log reduction means total kill of bacteria. Zero log reduction means some reduction of bacterial growth and extended contact causes further reduction. Washing tests were following AATCC-124 using machine washing warm (140° C.) for 15 min. and 90 grams of AATCC detergent 124.

Example VII

This example illustrates the durable press properties of Anti-2 finished fabrics.

Conc. of | Average Wrinkle Recovery Angle (degree)

| Anti-2 | Before washing | After 5 washing | After 10 washing | After 15 washing | After 20 washing | After 25 washing | After 30 washing |
|---|---|---|---|---|---|---|---|
| 0 | 87.0 | — | — | — | — | — | — |
| 2% | 88.3 | 97.2 | 100.4 | 96.0 | 97.8 | 103.0 | 99.2 |
| 6% | 115.4 | 111.8 | 108.4 | 111.2 | 111.0 | 111.2 | 109.8 |
| 10% | 120.0 | 117.8 | 114.8 | 112.1 | 114.8 | 113.8 | 112.7 |

Washing conditions were same as that in Example III and Example V.

Example VIII

This example illustrates the effects of pH and dipping time on biocidal activity.

Based on the proposed reaction mechanism, the modification reaction, i.e., the coupling reaction, prefers acidic conditions. As such, a lower pH is generally preferred during the finishing process. The reaction time also has an effect on the results of the chemical modification. The reaction time and pH values of finishing solutions were varied. Acidic conditions with lower pH values increased the pick-up rate of finishing agent by the finished fabrics, a finding which is consistent with the expected reaction mechanism. For instance, lowering the pH from 4.6 to 2.5 almost doubled the pick-up rates (Table VII). However, extended reaction times do not have any significant effect on the yields of the finishing fabrics.

TABLE VII

Biocidal Properties of Cotton Fabrics Processed Under Different pH's and Dipping Times

| pH | Dipping Time (min) | Pick-up rate % | Biocidal result against *E. Coli* after 1st wash | after 5 or 8 washes |
|---|---|---|---|---|
| 2.50 | 30 | 2.83 | >5 mm | kill all |
| 4.65 | 30 | 1.42 | >2 mm | >3 mm |
| 2.47 | 5 | 2.88 | >1 mm | kill all |
| 4.56 | 5 | 1.64 | >2 mm | >3 mm |

In addition, the finished fabrics were also tested in extensive washing tests. Generally, after 5–8 times of machine-washing according to AATCC Test Method 124, the fabrics were recharged with chlorine bleach and were tested against the bacteria. The disinfection distances of the samples still indicated that the fabrics finished under lower pH have strong bactericidal abilities.

Example IX

This example illustrates the breaking strength of the finished fabrics treated with Anti-1.

Table VIII indicates the breaking strength retention of the Anti-1 finished fabrics after extensive washes and regenerations of biocidal properties with different chlorine concentrations. The fabrics were finished in a solution with a concentration of 4% of monomethylol-5,5-dimethylhydantoin, and the take-up rate of the Anti-1 on the fabrics was 1.29%. Washing conditions were the same as in Table IV. Tensile strength of the fabrics were tested following American Society for Testing and Materials (ASTM) test method D1682. In the tests, a number of ravelled specimens with their long dimension parallel to filling of the fabrics was prepared in size of 25.4 mm×152.4 mm. Then, breaking load of the fabrics was recorded in pound (lb).

TABLE VIII

Breaking Strength Retention of Some Anti-1 Finished Fabrics

Breaking Strength, lb (% retention)

| Cl % | Fabric | Before | After treatment | After Bleach | After 5 washes + Bleach | After 10 washes + Bleach | After 15 washes + Bleach | After 20 washes + Bleach |
|---|---|---|---|---|---|---|---|---|
| 0.01 | #400 | 31.75 | 24.30 (77%) | 23.43 (74%) | 23.27 (73%) | 20.14 (63%) | 20.35 (64%) | 19.46 (61%) |
| | #7509 | 30.71 | 32.27 (100%) | 33.00 (100%) | 32.41 (100%) | 31.16 (100%) | 31.80 (100%) | 32.06 (100%) |
| 0.1 | #400 | 31.75 | 24.30 (77%) | 22.75 (74%) | 22.47 (74%) | 19.63 (62%) | 20.00 (63%) | 19.45 (61%) |
| | #7409 | 30.71 | 32.27 (100%) | 33.72 (100%) | 32.75 (100%) | 31.82 (100%) | 31.80 (100%) | 31.86 (100%) |
| 0.25 | #400 | 31.75 | 24.30 (77%) | 22.30 (70%) | 19.32 (61%) | 19.25 (61%) | 20.32 (64%) | 18.04 (60%) |
| | #7409 | 30.71 | 32.27 (100%) | 32.83 (100%) | 33.34 (100%) | 33.75 (100%) | 32.38 (100%) | 31.46 (100%) |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A process for preparing a microbiocidal cellulosic textile, said process comprising:
    (a) immersing a cellulosic textile in an aqueous treating solution which comprises a catalyst, a wetting agent and a heterocyclic amine;
    (b) removing the excess treating solution from said cellulosic textile;
    (c) drying said cellulosic textile;

(d) curing said dried cellulosic textile;

(e) washing said cured cellulosic textile to remove excess reagents;

(f) drying said cellulosic textile to remove water; and (g) treating said cellulosic textile with a halogenated aqueous solution to produce a heterocyclic N-halamine, thereby preparing a microbiocidal cellulosic textile.

2. The process of claim 1 wherein said cellulosic textile is cotton fabric.

3. The process of claim 2 wherein said cellulosic textile is a member selected from the group consisting of fabric, yarn and fiber.

4. The process of claim 1 wherein said heterocyclic amine is a member selected from the group consisting of monomethylol-5,5-dimethylhydantoin (MDMH), 1,3-dimethylol-5,5-dimethylhydantoin (DMDMH); monomethylolated and dimethylolated derivatives of 2,2,5,5-tetramethyl-1,3-imidazolidin-4-one, 6,6-dimethyl-1,3,5-triazine-2,4-dione, 4,4,5,5-tetramethyl-1,3-imidazolidin-2-one, cyanuric acid and 5,5-dimethylhydantoin; and monomethoxylated and dimethoxylated derivatives of monomethylolated and dimethylolated derivatives of 6,6-dimethyl-1,3,5-triazine-2,4-dione, 4,4,5,5-tetramethyl-1,3-imidazolidin-2-one, cyanuric acid, 5,5-dimethylhydantoin, 2,2,5,5-tetramethyl-1,3-imidazolidin-4-one and mixtures thereof.

5. The process of claim 1 wherein said heterocyclic amine is monomethylol-5,5-dimethylhydantoin (MDMH).

6. The process of claim 1 wherein said heterocyclic amine is 1,3-dimethylol-5,5-dimethylhydantoin (DMDMH).

7. The process of claim 1 wherein said catalyst is a member selected from the group consisting of magnesium salts, zinc salts and ammonium salts.

8. The process of claim 1 wherein said catalyst is a member selected from the group consisting of $MgCl_2$, $Mg(NO_3)_2$, $Zn(NO_3)_2$ and $NH_4NO_3$.

9. A process for preparing a microbiocidal cellulosic or other polymeric material textile having a reactive functional group, said process comprising:

(a) immersing a cellulosic or other polymeric material textile in an aqueous treating solution which comprises a catalyst, a wetting agent and a heterocyclic amine;

(b) removing the excess treating solution from said cellulosic or other polymeric material textile;

(c) drying said cellulosic or other polymeric material textile;

(d) curing said dried cellulosic or other polymeric material textile;

(e) washing said cured cellulosic or other polymeric material textile to remove excess reagents;

(f) drying said washed cellulosic or other polymeric material textile to remove water; and (g) treating said cellulosic or other polymeric material textile with a halogenated aqueous solution to produce a heterocyclic N-halamine, thereby preparing a microbiocidal cellulosic or other polymeric material textile.

10. The process of claim 9 wherein said cellulosic or other polymeric textile is cotton/polyester fabric.

11. The process of claim 9 wherein said heterocyclic amine is a member selected from the group consisting of monomethylol-5,5-dimethylhydantoin (MDMH), 1,3-dimethylol-5,5-dimethylhydantoin (DMDMH); monomethylolated and dimethylolated derivatives of 2,2,5,5-tetramethyl-1,3-imidazolidin-4-one, 6,6-dimethyl-1,3,5-triazine-2,4-dione, 4,4,5,5-tetramethyl-1,3-imidazolidin-2-one, cyanuric acid and 5,5-dimethylhydantoin; and monomethoxylated and dimethoxylated derivatives of monomethylolated and dimethylolated derivatives of 6,6-dimethyl-1,3,5-triazine-2,4-dione, 4,4,5,5-tetramethyl-1,3-imidazolidin-2-one, cyanuric acid, 5,5-dimethylhydantoin, 2,2,5,5-tetramethyl-1,3-imidazolidin-4-one and mixtures thereof.

12. The process of claim 9 wherein said heterocyclic amine is monomethylol-5,5-dimethylhydantoin (MDMH).

13. The process of claim 9 wherein said heterocyclic amine is 1,3-dimethylol-5,5-dimethylhydantoin (DMDMH).

14. A process for preparing a microbiocidal cellulosic article, wherein said article is a member selected from the group consisting of a surgeon's gown, a cap, a mask, a surgical cover, a patient drape, a carpeting, a bedding material, an underwear, a sock and a uniform, said process comprising:

(a) immersing a cellulosic article in an aqueous treating solution which comprises a catalyst, a wetting agent and a heterocyclic amine;

(b) removing the excess treating solution from said cellulosic article;

(c) drying said cellulosic article;

(d) curing said dried cellulosic article;

(e) washing said cured cellulosic article to remove excess reagents;

(f) drying said cellulosic article to remove water; and (g) treating said cellulosic article with a halogenated aqueous solution to produce a heterocyclic N-halamine, thereby preparing a microbiocidal cellulosic article.

15. The process of claim 14, wherein said cellulosic article is made of paper.

16. A process for preparing a microbiocidal cellulosic or polymeric article having a reactive functional group, wherein said article is a member selected from the group consisting of a surgeon's gown, a cap, a mask, a surgical cover, a patient drape, a carpeting, a bedding material, an underwear, a sock and a uniform, said process comprising:

(a) immersing a cellulosic or polymeric article in an aqueous treating solution which comprises a catalyst, a wetting agent and a heterocyclic amine;

(b) removing the excess treating solution from said cellulosic or polymeric article;

(c) drying said cellulosic or polymeric article;

(d) curing said dried cellulosic or polymeric article;

(e) washing said cured cellulosic or polymeric article to remove excess reagents;

(f) drying said washed cellulosic or polymeric article to remove water; and (g) treating said cellulosic or polymeric article with a halogenated aqueous solution to produce a heterocyclic N-halamine, thereby preparing a microbiocidal cellulosic or polymeric article.

* * * * *